United States Patent
Alazraki et al.

(10) Patent No.: US 9,301,119 B2
(45) Date of Patent: Mar. 29, 2016

(54) METHOD AND APPARATUS FOR PROVIDING EMERGENCY INFORMATION

(71) Applicant: MOTOROLA SOLUTIONS, INC, Schaumburg, IL (US)

(72) Inventors: Scott M Alazraki, Davie, FL (US); Lisajane M Romer, Delray Beach, FL (US); Daniel A Tealdi, Plantation, FL (US)

(73) Assignee: MOTOROLA SOLUTIONS, INC., Schaumburg, IL (US)

( * ) Notice: Subject to any disclaimer, the term of this patent is extended or adjusted under 35 U.S.C. 154(b) by 10 days.

(21) Appl. No.: 14/161,769

(22) Filed: Jan. 23, 2014

(65) Prior Publication Data

US 2015/0208221 A1  Jul. 23, 2015

(51) Int. Cl.
*H04M 11/04* (2006.01)
*H04W 4/22* (2009.01)
*G06F 19/00* (2011.01)
*H04M 3/51* (2006.01)
*H04W 4/00* (2009.01)

(52) U.S. Cl.
CPC ............ *H04W 4/22* (2013.01); *G06F 19/322* (2013.01); *H04M 3/5116* (2013.01); *H04M 11/04* (2013.01); *H04M 2242/04* (2013.01); *H04W 4/008* (2013.01)

(58) Field of Classification Search
CPC . H04W 4/22; H04W 52/0254; H04W 64/006; H04W 76/007; H04W 88/02
USPC ...................................................... 455/404.1
See application file for complete search history.

(56) References Cited

U.S. PATENT DOCUMENTS

| | | | |
|---|---|---|---|
| 8,521,122 B2 | 8/2013 | Scott et al. | |
| 8,830,054 B2* | 9/2014 | Weiss | 340/539.11 |
| 2005/0208925 A1* | 9/2005 | Panasik et al. | 455/404.1 |
| 2006/0230270 A1 | 10/2006 | Goffin | |
| 2006/0252998 A1* | 11/2006 | Kimbrell | 600/300 |
| 2007/0135043 A1 | 6/2007 | Hayes et al. | |
| 2007/0142026 A1* | 6/2007 | Kuz et al. | 455/404.1 |
| 2010/0240337 A1* | 9/2010 | DiMeo et al. | 455/404.1 |

(Continued)

FOREIGN PATENT DOCUMENTS

| | | |
|---|---|---|
| WO | 2007118331 A1 | 10/2007 |
| WO | 2013112571 A1 | 8/2013 |

OTHER PUBLICATIONS

Salvador Aguinaga, et al. "Method for Privacy-Protecting Display and Exchange of Emergency Information on Mobile Devices", IEEE, Dept of Computer Science and Engineering, Notre Dame, Indiana, 2012; 4 Pages.

(Continued)

*Primary Examiner* — Charles Appiah
*Assistant Examiner* — Jaime Holliday

(57) ABSTRACT

A method and apparatus for a device to provide emergency information is provided herein. During operation, an emergency responder will send out a wireless request for ICE information. Any device in the area will wirelessly respond to the request by providing ICE information, as long as a predetermined criterion is met. Because ICE information can be requested, and obtained wirelessly, a first responder does not need physical access to the device storing the ICE information. Thus, ICE information can be obtained from a device even when the device is not immediately accessible to the first responder.

11 Claims, 4 Drawing Sheets

(56) References Cited

U.S. PATENT DOCUMENTS

2012/0064855 A1* 3/2012 Mendelson ............... 455/404.2
2013/0040600 A1 2/2013 Reitnour et al.

OTHER PUBLICATIONS

Einstein Healthcare Network, ICE App for Phone; 3 Pages; Oct. 2013.

Emergency Link "In a Medical Crisis, Service Helps Others to Help You", Jun. 26, 2012; 5 Pages.
iTUNES Preview; ICE Pro Version by iHEALTH Ventures LLC; 3 Pages; Aug. 13, 2013.
PCT International Search Report Dated Apr. 8, 2015 for Counterpart Application PCT/US2015/011975.
EPO "Mitteilung Des Europischen Patentamts Vom 1. Oct. 2007" = Notice From the European Patent Office Dated Oct. 1, 2007 Concerning Business Methods.

* cited by examiner

METHOD AND APPARATUS FOR PROVIDING EMERGENCY INFORMATION

FIELD OF THE INVENTION

The present invention generally relates to providing emergency information to requesting devices, and more particularly to a method and apparatus for providing emergency information to requesting devices only when a predetermined condition is met.

BACKGROUND OF THE INVENTION

It is becoming more common for users of cellular telephones to store ICE (In Case of Emergency) information on their device. Such information comprises personal and medical information about an individual, such as names, contacts, telephone numbers, blood type, allergies, medications prescribed, existing medical conditions, health insurance provider, etc. ICE information stored on devices is meant to be obtained when the patient is unresponsive.

A problem exists for first responders in extracting ICE information when manual extraction through the device's user interface is not possible. For example, if a first responder cannot locate or cannot obtain access to a victim's cell phone (e.g., cell phone is somewhere in the vehicle but can't be easily found), it may be impossible to obtain ICE information for the victim. Therefore, a need exists for a method and apparatus for providing emergency information to a requesting device that allows ICE information to be obtained, even when a device is not immediately accessible.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required.

DETAILED DESCRIPTION

In order to address the above-mentioned need, a method and apparatus for a device to provide emergency information is provided herein. During operation, an emergency responder will send out a wireless request for ICE information, Any device in the area will wirelessly respond to the request by providing ICE information, as long as a predetermined criterion is met. Because ICE information can be requested, and obtained wirelessly, a first responder does not need physical access to the device storing the ICE information. Thus, ICE information can be obtained from a device even when the device is not immediately accessible to the first responder.

Expanding on the above, consider a situation where a first responder is sending out a broadcast message for devices within an area to provide ICE information. Such a message may comprise a simple message requesting ICE information that is transmitted using a short range communication system protocol, such as, but not limited to an 802.11 or Bluetooth protocol.

Since all devices within range of the requesting device will receive the request, it is advantageous to have only the desired device provide ICE information. In order to accomplish this, ICE information is provided by all devices hearing the request, as long as a predetermined criteria is met. The "predetermined criteria" is chosen so that the desired device will have a high probability of responding to the request, while unwanted devices will have a lower probability of responding to the request. For example, in a first embodiment, the predetermined criteria may be the detection of an accident (e.g., a fall, or an automobile accident) by the device. In a second embodiment, the predetermined criteria may comprise the passing of time after the request is sent without the user of the device opting out of the response.

Figure 1:
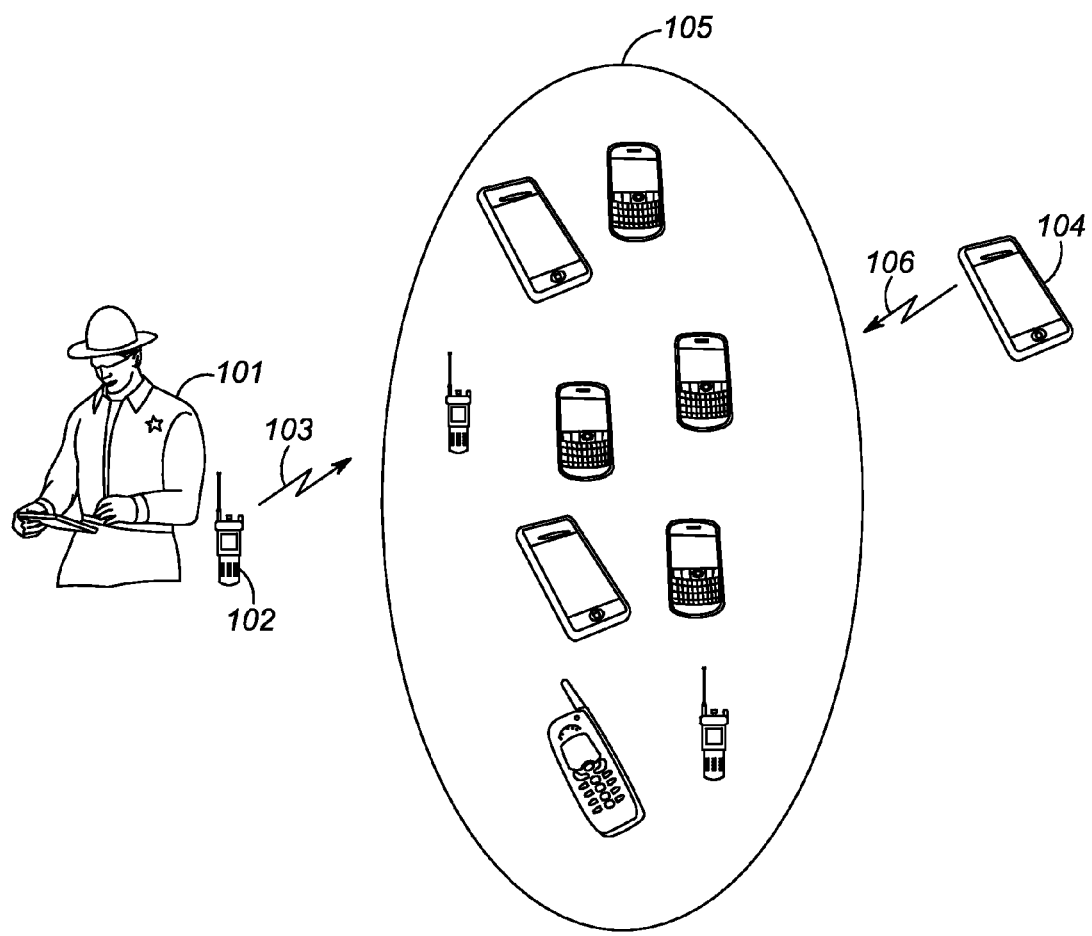
FIG. 1 is block diagram illustrating a general operational environment, according to one embodiment of the present invention.

FIG. 1 is block diagram illustrating a general operational environment, according to one embodiment of the present invention. The environment of FIG. 1 illustrates public-safety officer 101 at an incident scene. As is evident, many electronic devices 104-105 also exist at the scene. These electronic devices 104-105 may comprise electronic devices worn/operated by other public-safety officers, the general public, multiple victims, . . . , etc. Assume, in FIG. 1 that device 104 contains ICE information needed by officer 101. Officer 101 may instruct radio 102 to transmit request 103 for ICE information to all radios 104-105 within the general vicinity. Radio 104 may then respond with ICE information 106 that will be received and displayed by radio 102.

As discussed above, it is undesirable to have devices 105 respond to the request. In order to accomplish this, radios 104-105 will only respond to request 103 if a predetermined event or condition has been met.

Radio Responds when the Radio has Detected an Accident or Impact has Occurred

In a first embodiment radios 104-105 are equipped with context-aware circuitry, (e.g., accelerometers) to detect if a potential accident or impact has occurred. In the first embodiment of the present invention radios 104-105 will only respond if they have detected a potential accident or impact. For example, if radios 104-105 have detected a large force above a predetermined limit, they will respond to a request for ICE information. Assume that radio 104 has detected a potential accident or impact. Radio 104 will then enter an "automatic mode" of operation, automatically responding (for a predetermined time) to any ICE request 103 by wirelessly transmitting ICE information 106. If all other radios 105 have not experienced an accident or impact, they will fail to respond to ICE request 103.

It should be noted a user of devices 104-105 may have an option of disabling the auto response. For example, assume that the user of device 104 accidently dropped device 104.

The dropping of device 104 may cause device 104 to falsely detect a potential accident. In this situation, the user of device 104 may not want ICE information to be automatically provided to a requester. With this in mind, device 104 may provide a warning to the user that an accident has been detected and that auto-response has been activated. The user can then turn auto-response off if desired.

In an alternate embodiment, context-aware circuitry 207 does not need to be located within device 104. For example, an automobile may detect a crash, and provide this information to device logic circuitry 203.

Radio Responds to the ICE Request Unless a User has Instructed the Radio Otherwise In this particular embodiment, all devices 104-105 will automatically respond to request 103 unless the radio has been instructed otherwise. More particularly, all users of devices 104-105 will be given an indication that ICE information was requested from their device and will be provided to the requestor if they do not opt out. The users will be given a predetermined amount of time (e.g., 10 seconds) to opt out of providing ICE information. If devices 104-105 do not receive an opt-out, then ICE information will automatically be provided to the requester.

ICE Request Message and ICE Response Message

As discussed above, message 103 is sent to radios 104-105 requesting ICE information. Message 106 is sent in response to the received request. These messages are preferably sent using a Bluetooth communication system protocol. More particularly, (in the first embodiment) upon detection of an accident, the victims' device will automatically enter BLE "scanning" mode as described in the Bluetooth standard. In the second embodiment, the victims' device could always be in a BLE "scanning" mode. As part of scanning mode operation, device 104 scans for "advertisements" at a particular duty cycle. The ICE request can be sent as an "advertisement".

Upon detecting the advertisement, a validity check is performed (in the first embodiment—the previous accident/impact detection; in the second embodiment—not opting out) to ensure that the First Responder is retrieving ICE information only from those that they desire. The victim's device will then enter a "connecting" state, where the BLE wireless connection event state is set up (e.g., CONNECT_REQ could be used to transmit ICE information from device 104).

The Bluetooth communication system protocol could alternatively be set up with the victims' device as the advertiser and the First Responder device in a BLE scanning mode, to achieve the same end result of transferring the victims' ICE information from device 104. Additionally, initial discovery does not have to be limited to the described embodiments. For example, standard Bluetooth profiles like the Find Me profile or the Proximity profile could be leveraged as well to establish the initial discovery and connectivity.

Figure 2:
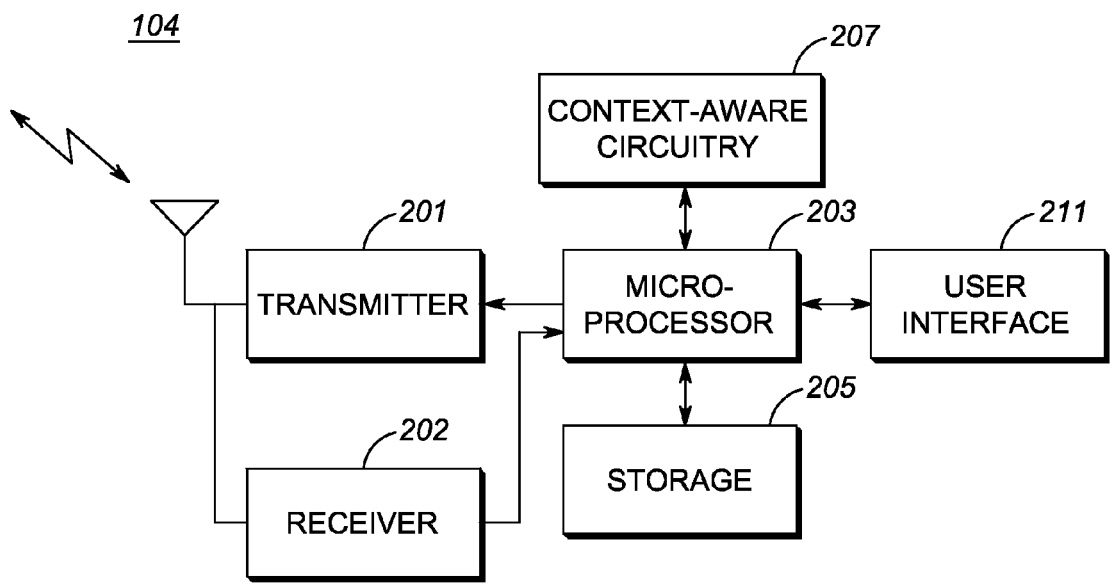
FIG. 2 is a block diagram of a radio of FIG. 1.

FIG. 2 is a block diagram of radio 104. Radio 104 typically comprises processor 203 that is communicatively coupled with various system components, including transmitter 201, receiver 202, general storage component 205, optional context-aware circuitry 207, and potentially, a user interface (GUI) 211. Only a limited number of system elements are shown for ease of illustration; but additional elements may be included in the radio 104.

Figure 3:
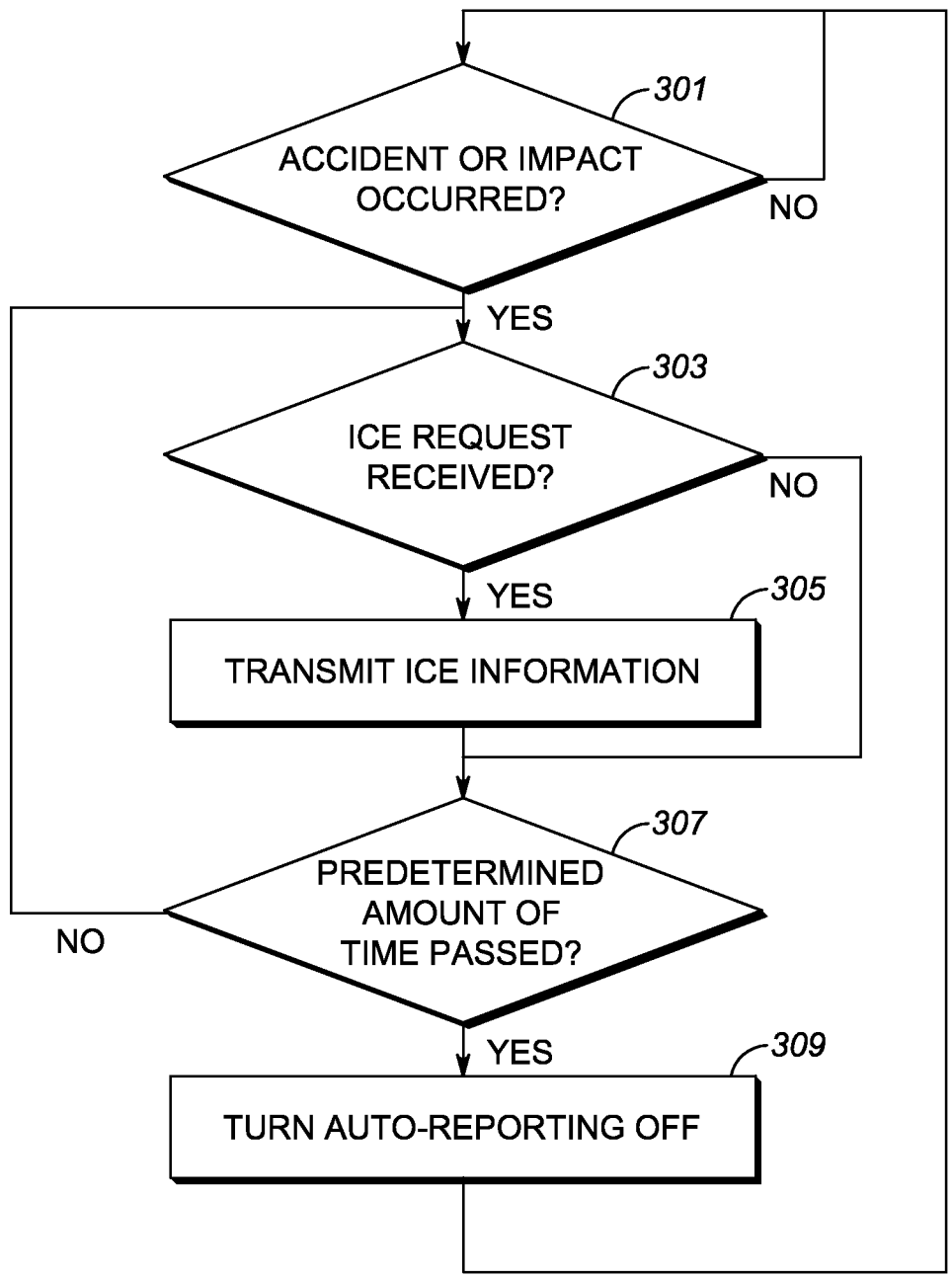
FIG. 3 is a flow chart of the radio of FIG. 3 in accordance with a first embodiment of the present invention.
Figure 4:
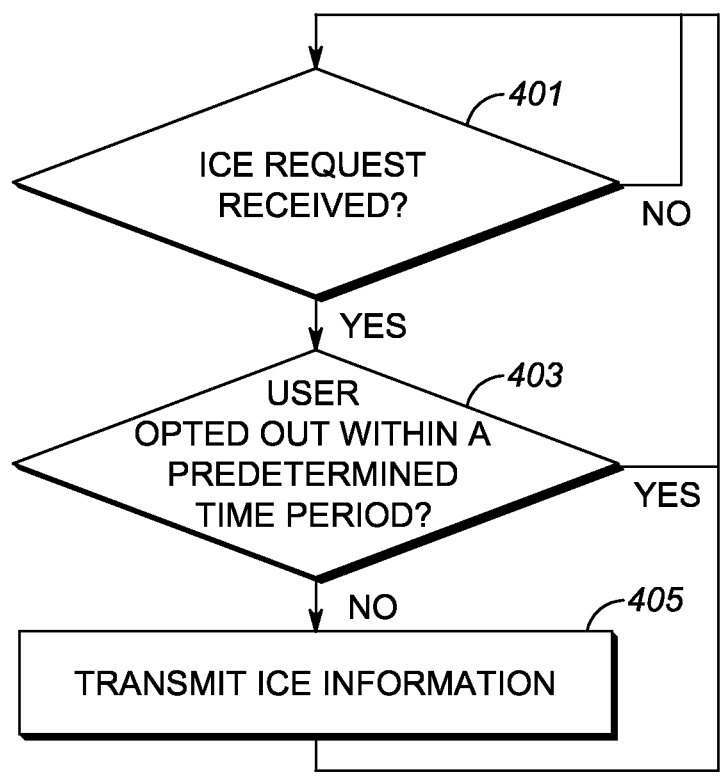
FIG. 4 is a flow chart of the radio of FIG. 3 in accordance with a second embodiment of the present invention.

Processing device 203 may be partially implemented in hardware and, thereby, programmed with software or firmware logic or code for performing functionality described in FIG. 3 and FIG. 4; and/or the processing device 203 may be completely implemented in hardware, for example, as a state machine or ASIC (application specific integrated circuit).

Storage 205 can include short-term and/or long-term storage of ICE information, Storage 205 may further store software or firmware for programming the processing device 203 with the logic or code needed to perform its functionality.

User interface 211 provides a way of conveying information to, and receiving information from, a user of device 104. In particular, user interface 211 may include a keypad, a display/monitor, a mouse/pointing means, and/or various other hardware components to provide a man/machine interface. As one of ordinary skill in the art will recognize, ICE information may be initially input by the user via interface 211, and ultimately stored in storage 205. In addition, user interface 211 may provide the user with a warning that ICE information is going to be provided unless an "opt out" is received. User interface 211 may receive the "opt out" instruction from the user.

When operating in accordance with the first embodiment, context-aware circuitry 207 preferably comprises an accelerometer, however in alternate embodiments circuitry 207 may comprise any device capable of generating information used to detect a potential accident. For example, context-aware circuitry 207 may comprise a smoke detector, a fire detector, a water detector, an impact detector, a biometric sensor, etc. Regardless of the makeup of context-aware circuitry 207, logic circuitry 203 will use information generated by circuitry 207 to determine if an accident has occurred.

Transmitter 201 and receiver 202 are common circuitry known in the art for communication utilizing a well known communication protocol, and serve as means for transmitting and receiving messages. For example, receiver 202 and transmitter 201 may be well known long-range or short-range transceivers that utilize such protocols as Apco 25 (Project 25) communication system protocol, IEEE 802.11 communication system protocol, Bluetooth, Bluetooth Low Energy, HyperLAN, or any other communication system protocol. Radio 104 may contain multiple transmitters and receivers, to support multiple communications protocols.

In the first embodiment processor 203 receives a notification from context-aware circuitry 207 that an event or condition has occurred. Upon receiving the notification, processor 203 will assume an accident or impact has occurred. Such events or conditions may comprise:

- circuitry 207 detecting a force in excess of a threshold (e.g., 7 G);
- circuitry 207 detecting excessive smoke;
- circuitry 207 detecting excessive heat;
- circuitry 207 detecting water;
- circuitry 207 detecting that a vehicle collision/accident has occurred;
- circuitry 207 detecting sudden and/or excessive rotation;
- circuitry 207 detecting lack of motion;
- circuitry 207 acting as a biosensor detecting heart rate, breathing rate, or other biosensor reading, etc. above/below a predetermined threshold;
- circuitry 207 acting as a timer, detecting a period of time having elapsed since receiving the ICE request.

When processor 203 is notified of any of the above, processor 203 assumes an accident has occurred. ICE information will automatically be provided upon request.

In a first embodiment, the apparatus of FIG. 2 comprises a receiver receiving a request for ICE information, context-aware circuitry detecting an accident/impact has occurred, a transmitter, and logic circuitry instructing the transmitter to transmit ICE information in response to the request, automatically, and based upon the detection that an accident/impact has occurred.

In a second embodiment, the apparatus of FIG. 2 comprises a receiver receiving a request for ICE information, context-aware circuitry detecting a period of time has elapsed since the request was received, a user interface, a transmitter, and logic circuitry instructing the transmitter to transmit ICE information in response to the request, automatically, and based upon the period of time and whether or not a opt-out was received from the user interface.

FIG. 3 is a flow chart showing operation of the radio of FIG. 3 in accordance with a first embodiment of the present invention. In this particular embodiment, ICE information will be provided automatically and wirelessly upon the detection of an accident or impact (predetermined event). The logic flow in FIG. 3 assumes that automatic ICE response is turned off entering step 301.

The logic flow begins at step 301 where context-aware circuitry 207 determines/detects if an accident or impact has occurred and provides this determination to logic circuitry 203. If at step 301, an accident or impact was detected, the logic flow continues to step 303 where logic circuitry 203 determines if a request for ICE information was received via wireless receiver 202. If so, the logic flow continues to step 305 where ICE information is received from storage 205 and transmitted via transmitter 201. The logic flow then continues to step 307 where it is determined if a predetermined amount of time has occurred since the accident or impact was detected. If so, the logic flow continues to step 309 where automatic ICE response is turned off and the logic flow returns to step 301. If, however, at step 307 it has been determined that a predetermined amount of time has not occurred, the logic flow returns to step 303, where ICE information is provided upon request. In the above logic flow, the "predetermined amount of time" may comprise a few minutes, hours, days, or longer.

FIG. 4 is a flow chart showing operation of the radio of FIG. 2 in accordance with a second embodiment of the present invention. In this particular embodiment, ICE information will be provided wirelessly upon a user not opting out (predetermined event). The logic flow in FIG. 4 assumes that automatic ICE response is turned off entering step 401.

The logic flow begins at step 401 where logic circuitry 203 determines if an ICE request was received via wireless receiver 202. If so, the logic flow continues to step 403 where logic circuitry 203 determines if the user has opted out within a predetermined period of time (e.g., 5 seconds). In this embodiment, a user may opt out of an automatic response via user interface 211. More particularly, once an ICE request is received, a notification of the request may be provided to the user via user interface 211, along with text asking if the user would like to opt out of the auto-response. Using interface 211, the user may opt out.

If, at step 403, it has been determined that the user opted out within a predetermined period of time, the logic flow returns to step 401, otherwise the logic flow continues to step 405 where ICE information is received from storage 205 and transmitted via transmitter 201. The logic flow then returns to step 401. As discussed above, in this embodiment the "predetermined period of time" may comprise a short period of time, for example 10 seconds. Thus, when an ICE request is received, a user will be given, for example, 10 seconds to opt out of an automatic response. If the "opt out" has not been received, ICE information will automatically be provided to the requester.

The logic flow of FIG. 3 and FIG. 4 result in a method of operating device 104 that determines if a condition is met. As discussed, the condition is taken from the group consisting of context-aware circuitry detecting an accident/impact or a user not opting out of an automatic ICE response. ICE information is only transmitted when the condition is met.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

Those skilled in the art will further recognize that references to specific implementation embodiments such as "circuitry" may equally be accomplished via either on general purpose computing apparatus (e.g., CPU) or specialized processing apparatus (e.g., DSP) executing software instructions stored in non-transitory computer-readable memory. It will also be understood that the terms and expressions used herein have the ordinary technical meaning as is accorded to such terms and expressions by persons skilled in the technical field as set forth above except where different specific meanings have otherwise been set forth herein.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method for operating a cellular telephone, the method comprising the steps of:
   determining if context-aware circuitry has detected an accident/impact;
   receiving a request from an emergency responder for in-case of emergency (ICE) information using a Bluetooth communication protocol;
   not sending the ICE information over the Bluetooth communication protocol when the request has been received from the emergency responder based on a fact that the context-aware circuitry has not detected the accident/impact.

2. The method of claim 1 wherein the step of receiving the request comprises the step of receiving the request wirelessly.

3. The method of claim 1 wherein the step of determining if the accident/impact has been detected comprises the step of the context-aware circuitry determining at least one of the following:
   detecting a force in excess of a threshold;
   detecting excessive smoke;
   detecting excessive heat;
   detecting water;
   detecting that a vehicle collision/accident has occurred;
   detecting sudden and/or excessive rotation;
   detecting lack of motion;
   detecting heart rate or a breathing rate or other biosensor reading, above or below a predetermined threshold;
   detecting that a period of time has elapsed since receiving the ICE request.

4. The method of claim 1 further comprising the step of:
   entering a Bluetooth scanning mode upon the detection of the accident/impact; and
   wherein the request is received as an advertisement during the Bluetooth scanning mode.

5. The method of claim 1 wherein the request is received as an advertisement during the Bluetooth scanning mode.

6. A cellular telephone comprising:
   context-aware circuitry detecting if an accident/impact has occurred;
   a receiver receiving a request from an emergency responder for ICE information using a Bluetooth communication protocol;
   a transmitter; and
   logic circuitry instructing the transmitter to transmit ICE information using the Bluetooth communication protocol only in response to the received request and upon the detection that an accident/impact has occurred, otherwise not instructing the transmitter to transmit the ICE information over the Bluetooth communication protocol based on a fact that the context-aware circuitry has not detected the accident/impact and the request for ICE information has been received.

7. The apparatus of claim 6 wherein:
   the receiver comprises a wireless receiver; and
   the transmitter comprises a wireless transmitter.

8. The cellular telephone of claim 6 wherein the receiver enters a Bluetooth scanning mode upon the detection of the accident/impact; and
   wherein the request is received as an advertisement during the Bluetooth scanning mode.

9. A cellular telephone comprising:
   a receiver receiving a request from an emergency responder for ICE information;
   context-aware circuitry determining a period of time since the request was received and determining if an accident/impact has occurred; a user interface;
   a transmitter using the Bluetooth protocol; and
   logic circuitry instructing the transmitter to transmit ICE information using the Bluetooth protocol in response to the request only when the accident/impact has been detected and based upon the period of time and whether or not an opt-out was received from the user interface, otherwise not instructing the transmitter to transmit the ICE information over the Bluetooth communication protocol based on a fact that the context-aware circuitry has not detected the accident/impact and the request for ICE information has been received.

10. The apparatus of claim 9 wherein:
    the receiver comprises a wireless receiver; and
    the transmitter comprises a wireless transmitter.

11. The cellular telephone of claim 9 wherein the receiver enters a Bluetooth scanning mode upon the determination that the accident/impact has occurred; and
    wherein the request is received as an advertisement during the Bluetooth scanning mode.

* * * * *